United States Patent [19]

Schrenker

[11] Patent Number: 4,624,625

[45] Date of Patent: Nov. 25, 1986

[54] HIGH PRESSURE METERING PUMP

[75] Inventor: Helge Schrenker, Karlsruhe, Fed. Rep. of Germany

[73] Assignee: Hewlett-Packard Company, Palo Alto, Calif.

[21] Appl. No.: 712,332

[22] Filed: Mar. 14, 1985

Related U.S. Application Data

[63] Continuation of Ser. No. 426,047, Sep. 28, 1982, abandoned.

[30] Foreign Application Priority Data

Oct. 8, 1981 [DE] Fed. Rep. of Germany ....... 3139925

[51] Int. Cl.$^4$ ............................................. F04B 49/06
[52] U.S. Cl. ........................................ 417/20; 417/44; 417/298; 417/317; 417/540
[58] Field of Search ............... 417/297, 298, 317, 505, 417/540, 18, 20, 44

[56] References Cited

U.S. PATENT DOCUMENTS

| | | | |
|---|---|---|---|
| 3,653,783 | 4/1972 | Sauder | 417/505 X |
| 3,855,129 | 12/1974 | Abrahams et al. | 417/38 X |
| 3,917,531 | 11/1975 | Magnussen | 210/101 |
| 4,003,679 | 1/1977 | McManigill | 417/388 X |
| 4,045,343 | 8/1977 | Achener et al. | |
| 4,128,476 | 12/1978 | Rock | 210/31 |
| 4,131,393 | 12/1978 | Magnussen | 417/22 |
| 4,137,011 | 1/1979 | Rock | 417/22 |
| 4,180,375 | 12/1979 | Magnussen | 417/22 |
| 4,245,963 | 1/1981 | Hutchins et al. | 417/540 X |
| 4,297,083 | 10/1981 | Von Petery | 417/505 X |
| 4,389,163 | 6/1983 | Magnussen et al. | 417/2 |
| 4,492,524 | 1/1985 | Koch et al. | 417/18 |

FOREIGN PATENT DOCUMENTS

| | | |
|---|---|---|
| 2263768 | 11/1974 | Fed. Rep. of Germany. |
| 44486 | 4/1981 | Japan ................................. 417/317 |
| 426068 | 10/1974 | U.S.S.R. ............................ 417/317 |

Primary Examiner—Leonard E. Smith
Attorney, Agent, or Firm—Douglas A. Kundrat

[57] ABSTRACT

A high pressure metering pump has a duty cycle consisting of an aspiration portion where liquid is aspirated into a pumping chamber, a compression portion where the aspirated liquid is compressed to feed pressure, a feed portion where a part of the compressed liquid is expelled out of the pumping chamber, and a decompression portion where the liquid remaining in the pumping chamber is expanded to aspiration pressure. A measurement and control apparatus for the pump comprises a controller for adjusting and keeping constant the mean flow rate of the pumped liquid on the aspiration side or on the high pressure side of the pump. The apparatus further comprises a detector for detecting the transition point between the compression and feed portions and/or between the decompression and aspiration portions. The detector derives a control signal for the pump speed and for the optimal opening instant of an externally actuated input valve of the pump from the phase relationships of said transitions.

11 Claims, 4 Drawing Figures

HIGH PRESSURE METERING PUMP

CROSS REFERENCE TO RELATED APPLICATION

This application is a continuation of application Ser. No. 426,047, filed Sept. 28, 1982, now abandoned.

BACKGROUND OF THE INVENTION

High pressure piston and piston/diaphragm metering pumps constructed according to the prior art are often unsuited for many high performance liquid chromatography uses because their mean flow rate, $\overline{V}$ (mean pumped liquid volume per unit of time), is dependent on feed pressure and on the nature and composition of the pumped liquid. This dependence is due to the compressibility $\mathcal{æ}$ of the pumped liquid and to the resilience of the pump elements involved. Further, in piston/diaphragm pumps, wherein movement of the working piston is transmitted via a working liquid to a flexible diaphragm and therefrom to the pumping chamber, the compressibility of the working liquid must be taken into account. At a given feed pressure a certain portion of the piston stroke is used solely for compressing the aspirated liquid up to feed pressure (compression portion). Thus, the feed pumping portion of the stroke is delayed by a phase angle $\phi_1$ from bottom dead center of the driving crank. At this phase angle $\phi_1$ the output valve of the pump opens and the feed portion then lasts until driving crank top dead center (phase angle $\pi$). On the other hand, the aspiration portion does not start immediately after top dead center but, instead, is delayed by a phase angle $\phi_2 (>\pi)$. This delay is caused by expansion of the remaining liquid volume in the pumping chamber and the removal of stress from the pump elements (decompression portion).

The fractions of the total piston movement comprising the compression and decompression portions differ one from the other mainly because of the different volumes of liquid present in the pumping chamber at the beginning of each of said portions. When the driving crank is at bottom dead center, i.e., at the beginning of the compression portion, the total volume of liquid present in the pumping chamber is the sum of the piston stroke volume $V_d$ and the residual volume $V_o$ which remains in the pumping chamber after the end of a feed portion. The liquid volume to be compressed to the feed pressure, p, is therefore $V_o+V_d$. On the other hand, when the driving crank is at top dead center, i.e., at the beginning of the decompression portion, only the residual volume $V_o$ is present in the pumping chamber. Thus, the total liquid volume to be decompressed from feed pressure to aspiration pressure is only $V_o$. The influence of any resilient mechanical elements and the working liquid, however, should be equal during the compression and decompression portions. Nevertheless, $\phi_2$ cannot be directly computed from a known $\phi_1$ because the ratio of the two phase angles is also dependent on the compressibility $\mathcal{æ}$ of the pumped liquid. In the common case of variable liquid mixtures, the compressibility $\mathcal{æ}$ is dependent on the mixing ratio and properties of the liquid components and also on the feed pressure. Thus, compressibility is not a term which is known or can be assumed to be substantially constant.

For high performance liquid chromatography it is essential that a constant flow rate be maintained independent of feed pressure and the kind and composition of the pumped liquid since the accuracy of the analysis is substantially determined by the accuracy of the flow rate.

According to the prior art, various measurement and control apparatus for metering pumps have been proposed for generating constant and reproducible flow rates independent of high counter pressure, feed pressure, and the kind and composition of the pumped liquid. These prior art measurement and control apparatus can be roughly classified into the following six methods:

(1) Measuring the input or output flow of the pump, comparing the measurement with a predetermined nominal value and correcting the pump adjustment via a control loop consisting of measuring arrangement, comparator, adjusting element and pump. Such arrangements are described, e.g., in U.S. Pat. No. 3,917,531 and in German Pat. No. 2,263,768. These arrangements are disadvantageous in that they are expensive and often require calibration of indirect measuring devices.

(2) Keeping the feed pressure constant by means of a pressure control arrangement independent of the magnitude of flow resistances behind the pump. Such an arrangement is described in Varian Associates publication No. 03-913807-00, published in June, 1978. In such a feed arrangement the effect of a variable feed pressure upon the flow rate is fully avoided but the effect of the compressibility of the pumped liquid is still present. Therefore, in analyses which require programmable variation of the solvent composition a certain flow rate variation is encountered because of the varying compressibility of the pumped liquid.

(3) Continuously measuring the feed pressure downstream from the output valve and increasing the piston frequency as feed pressure increases in order to compensate for the increased liquid compression. See U.S. Pat. No. 3,855,129. This method is disadvantageous in that an individual calibration is necessary for each liquid used and in that the compensation is incomplete when liquid mixtures of varying composition are used.

(4) Using dual piston pumps with one pumping chamber delayed $\pi$ radians behind the other. In such an arrangement, as described in U.S. Pat. No. 4,137,011, each compression portion of the stroke appears as a fast pressure breakdown which is smoothed by a strong acceleration of the drive during each compression portion. Thus, durations of the compression portions and their contributions to the liquid flow are substantially reduced. By means of additional memory and regulating devices the nominal value for the pressure regulation is automatically adjusted when the flow resistances change. With this arrangement the mean feed flow rate $\overline{V}_p$, measured at feed pressure, may be kept substantially constant. However, it is often desired in liquid chromatography to keep the mean aspiration flow rate, $\overline{V}_o$, measured at intake pressure, constant because of the direct influence of this flow rate on the quantitative analysis result. To a first approximation the relationship $$\overline{V}_p = \overline{V}_o(1-\mathcal{æ}p)$$

exists between the two flow rates. Therefore, even though $\overline{V}_p$ is held constant, there is still a variation of $\overline{V}_o$ because of the feed pressure p and the compressibility $\mathcal{æ}$ of the pumped liquid.

(5) Using two separate pumps to independently control both the mean aspiration flow rate, $\overline{V}_o$, and the pumping pressure p. Examples of such arrangements are described in U.S. Pat. No. 4,003,679 and in U.S. Pat. No. 4,489,163. These references describe a series connection of a metering pump operating at nearly zero pressure and a high pressure pump. The high pressure pump is designed to pressurize all of the liquid delivered by the metering pump to the pressure necessary to overcome the flow resistances beyond the pump. Alternatively, a control element is located between the metering pump and the high pressure pump, said control element regulating the high pressure pump in such a manner that the amount of liquid flowing between the two pumps is equalized. Both arrangements fulfill the requirement for a constant mean aspiration flow rate $\overline{V}_o$, but are disadvantageous in that two pumps, instead of one, are required.

(6) Measuring the difference between the internal pressure in the pumping chamber and the feed pressure and moving the piston with a constant linear velocity corresponding to the required flow rate when the difference is zero while at all other times the piston is driven at the highest possible speed. See, e.g., U.S. Pat. No. 4,180,375. Thus, a constant flow rate with regard to the actual feed pressure is achieved. However, this method does not allow the generation of a constant flow rate with regard to decompressed liquid.

An additional use of metering pumps is the generation of mixing gradients, i.e., the controlled change of the composition of a solvent mixture with time. In liquid chromatography this is called gradient elution. The requirements for reproducibility and accuracy of the gradient function are as strict as the requirements for the flow rate during gradient elution.

A technically complicated and expensive arrangement for gradient elution which is known in the prior art comprises the use of a separate metering pump with programmable flow rate for each liquid component. A less expensive prior art arrangement is one wherein the liquid components delivered on the aspiration side of the pump are alternated under program control during the aspiration phase of the pump by means of proportioning valves in the aspiration tube. In this arrangement it is necessary to take into account the decompression portion in the control of the proportioning valves. In prior art method (2), described hereinabove, the input valve is synchronized with the pump drive in such a manner that it opens a constant phase angle $\phi$ after bottom dead center. The beginning of the proportioning valve control cycle is synchronized with the opening time of the input valve (see, e.g., German patent application No. 2,649,593). Since the delay phase angle is not automatically adjustable, this synchronization can be correct only for a specific compressibility $æ$ of the pumped liquid.

U.S. Pat. No. 4,128,476, mentioned above with reference to prior art method (4), shows a method wherein the times of the pressure breakdown minima are used as an indicator of the duration of the compression portion. Synchronization of the proportioning valves is accomplished by multiplying the angular duration of the compression portion by a constant which represents the decompression/compression time ratio. However, this synchronization can be correct only for an average compresssibility of the pumped liquid; if the real compressibility differs from this average errors may occur in the synchronization.

SUMMARY OF THE INVENTION

A high pressure metering pump has a duty cycle which includes: an aspiration portion, wherein liquid is aspirated into a pumping chamber; a compression portion, wherein the aspirated liquid is compressed to pumping pressure; a feed portion, wherein a part of the compressed liquid is expelled out of the pumping chamber; and, a decompression portion, wherein the liquid remaining in the pumping chamber is expanded to aspiration pressure. In accordance with the illustrated embodiment of the present invention, a measurement and control apparatus enables a one-stage high pressure metering pump to maintain a constant mean aspiration flow rate, $\overline{V}_o$, and to generate an accurate gradient elution independent of counter pressure and of the nature of the pumped liquid. The apparatus includes a controller for holding constant the mean flow rate of the pumped liquid and a detector for detecting the transition point between the compression and pumping portions and/or between the decompression and aspiration portions. The controller generates a signal for controlling the pump speed from the phase relationship(s) at said transition(s).

In accordance with the preferred embodiment, the angular durations of the decompression and compression portions of the full duty cycle (one full crank shaft rotation) are measured and control signals are derived therefrom. By using the measured value of the angular duration of the decompression portion (phase angle $\phi_2$), the mean aspiration flow rate $\overline{V}_o$ of the uncompressed liquid is kept constant. Alternatively, by using the measured value of the angular duration of the compression portion (phase angle $\phi_1$) the mean feed flow rate $\overline{V}_p$ of the liquid compressed to pumping pressure can be kept constant.

From the value of $\phi_2$, characterizing the angular duration of the decompression portion, a signal for electromagnetically or pneumatically opening (at $\phi_2$) and closing (at $2\pi$) a controlled input valve of the pump may be derived. Use of the externally controlled input valve avoids the contaminant and gas bubble performance problems associated with the prior art use of liquid flow actuated valves. Furthermore, a synchronizing signal may be derived from $\phi_2$ for controlling proportioning valves in the aspiration tube for gradient elution with pressure and compressibility compensation.

Once $\phi_1$ and $\phi_2$ are known the timing of the duty cycle may be optimized with regard to favorable conditions for the control of the proportioning valves on the one hand and the damping of liquid flow pulsations on the other hand.

The ratio between compression portion angular duration $\phi_1$ and decompression portion angular duration $\phi_2 - \pi$ may be used for continuous control of correct pump operation. In particular, the ratio may be used for detecting leakage at the input and output valves and for detecting the occurrence of air bubbles in the pumping chamber during the aspiration portion. If a pulsation damper is provided on the pressure side of the pump the ratio may be utilized to maintain the average volume on the pressure side of the pump constant at a given flow rate independent of feed pressure.

DESCRIPTION OF THE PREFERRED EMBODIMENT

Figure 1:
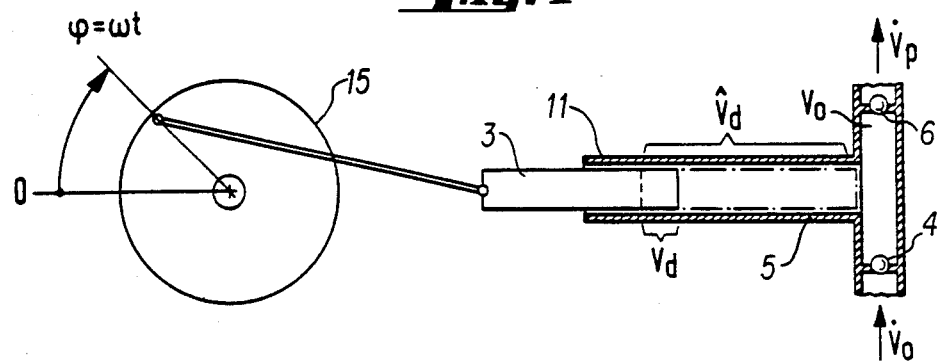
FIG. 1 is a schematic representation of a piston pump.
Figure 2:
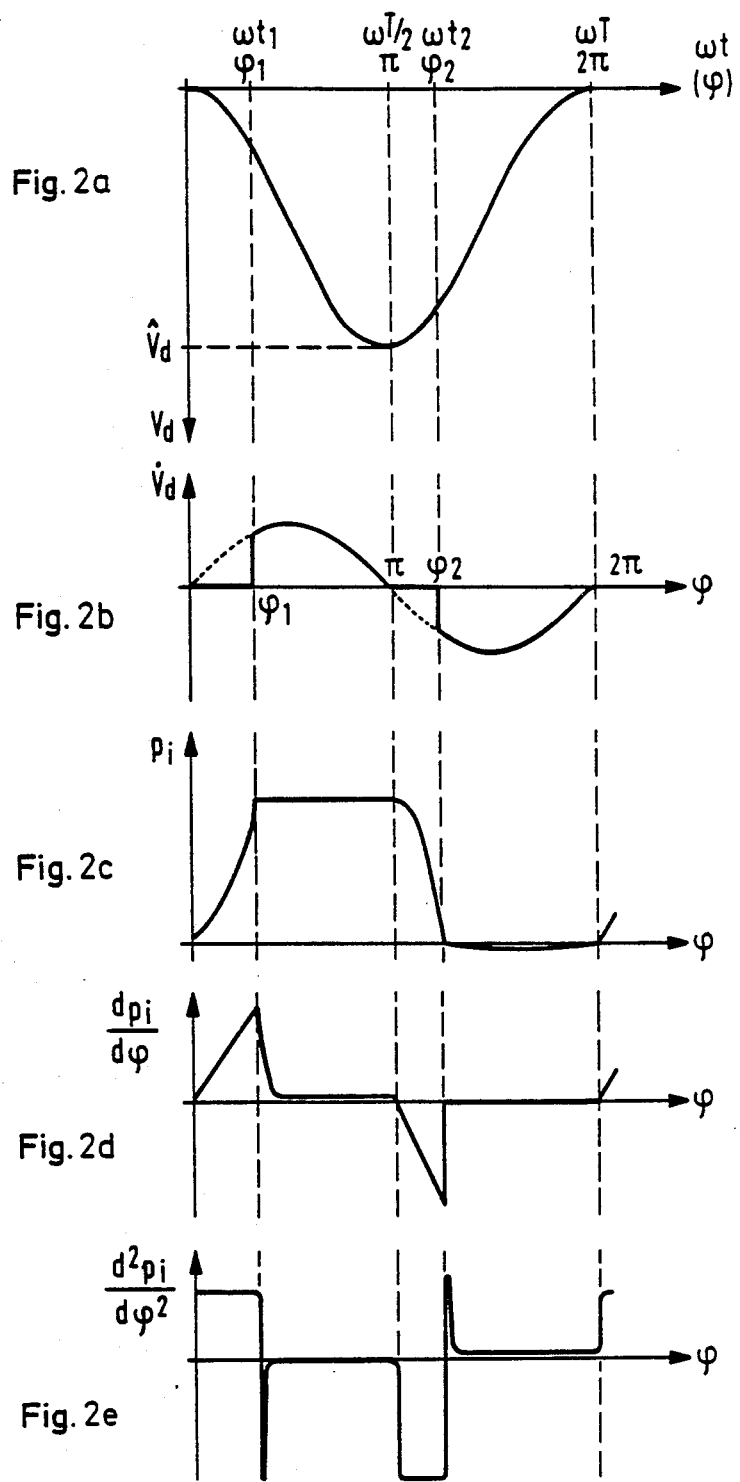
FIGS. 2a–e provide a graphical representation of selected parameters which characterize the operation of the pump depicted in FIG. 1.

FIG. 1 shows a well known pump 11 having a crankshaft 15 connected to piston 3. Liquid enters pump 11 through intake valve 4, is pressurized in cylinder 5, and is expelled from output valve 6. In FIG. 1, $\phi = \omega t$ represents the phase angle of crankshaft 15, $\omega$ is the angular velocity of crankshaft 15, $\hat{V}_d$ is the displacement volume of piston 3, $V_d$ is the stroke volume of piston 3, $\dot{V}_o$ is the residual volume of pump 11, $\dot{V}_o$ is the momentary aspiration flow rate of the uncompressed liquid, and $\dot{V}_p$ is the momentary feed flow rate of the liquid compressed to feed pressure p. The displacement volume, $V_d$ amounts to $$V_d = 0.5 \hat{V}_d (1 - \cos \phi).$$

and is depicted in FIG. 2a. The momentary feed flow rate, $\dot{V}_d$, initiated by piston 3 is depicted in FIG. 2b and is defined as $$\dot{V}_d = 0.5 \hat{V}_d \sin \phi,$$

when $\phi_1 \leq \phi \leq \pi$ (feed portion) or $\phi_2 \leq \phi \leq 2\pi$ (aspiration portion) or, respectively, when $t_1 \leq t \leq T/2$ and $t_2 \leq t \leq T$ (FIG. 2b), where the compression portion lasts from 0 to $\phi_1$ radians and the decompression portion lasts from $\pi$ to $\phi_2$ radians.

For applications in liquid chromatography the mean aspiration flow rate $\overline{V}_o$ of the uncompressed liquid is important. Only this flow rate is discussed below although the mean feed flow rate $\overline{V}_p$ of the compressed liquid can also be adjusted and kept constant in a similar manner.

The liquid volume aspirated by pump 11 during an entire cycle T is $$-V_{oi} = \int_{\phi_2}^{2\pi} 0.5 \, \hat{V}_d \sin \phi = 0.5 \, \hat{V}_d (\cos \phi_2 - 1)$$

Hence, the mean aspiration flow rate $\dot{V}_o$ averaged over the duration T is $$-\dot{V}_o = \frac{V_{oi}}{T} = \frac{0.5 \, \hat{V}_d}{T} (\cos \phi_2 - 1)$$

Thus, the duration T of the entire cycle necessary for generating a defined mean aspiration flow rate $\dot{V}_o$ is $$T = \frac{0.5 \, \hat{V}_d}{\dot{V}_o} (1 - \cos \phi_2) \quad (1)$$

Equation (1) is the control algorithm for maintaining a constant mean aspiration flow rate $\overline{V}_o$ and requires continuous measurement of $\phi_2$. FIGS. 2c–e depict the internal pressure, $p_i$, of the liquid within cylinder 5 and the first and second time derivatives thereof as functions of phase angle $\phi$. FIGS. 2c–e illustrate the measurement of phase angles $\phi_1$ and $\phi_2$. The signal obtained from the second derivative $\ddot{p}_i$ of the internal pressure $p_i$ (as measured with a suitable pressure detector) shows a very steep slope with changing sign at the transition between the decompression and aspiration portions ($\phi_2$) and at the transition between the compression and feed portions ($\phi_1$). Measurement of the instant in time at which this occurs identifies the required phase angles $\phi_1$ and $\phi_2$ when the instant in time is correlated with the instantaneous angular position $\phi(t)$ of crankshaft 15 as measured with a shaft encoder.

Besides being useful in the control algorithm for pump 11 and for controlling input valve 4 thereof, the value of $\phi_2$ is useful as a synchronizing signal for controlling proportioning valves in the aspiration tube of pump 11 leading to input valve 4 for generating mixing gradients, e.g., consisting of two components A and B. If, by means of the proportioning valve arrangement, the aspiration side of the pump is connected to a supply vessel for component A starting with crankshaft 15 angular position $\phi_2$ and is connected to a supply vessel for component B starting with crankshaft 15 angular position $\phi_3$, then the following relationship is valid for the average percentage of component B in the mixture (A+B)

$$\% B = \frac{\cos \phi_3 - 1}{\cos \phi_2 - 1} \cdot 100$$

The valve switching point necessary for generating a defined average mixing ratio % B in (A+B) is:

$$\phi_3 = -\arccos\left[\frac{\% B (\cos \phi_2 - 1)}{100} + 1\right] + 2\pi \quad (2)$$

This is the control algorithm necessary for controlling a valve proportioning arrangement for two components A and B which, of course, may be expanded to an arrangement for three or more components.

Figure 3:
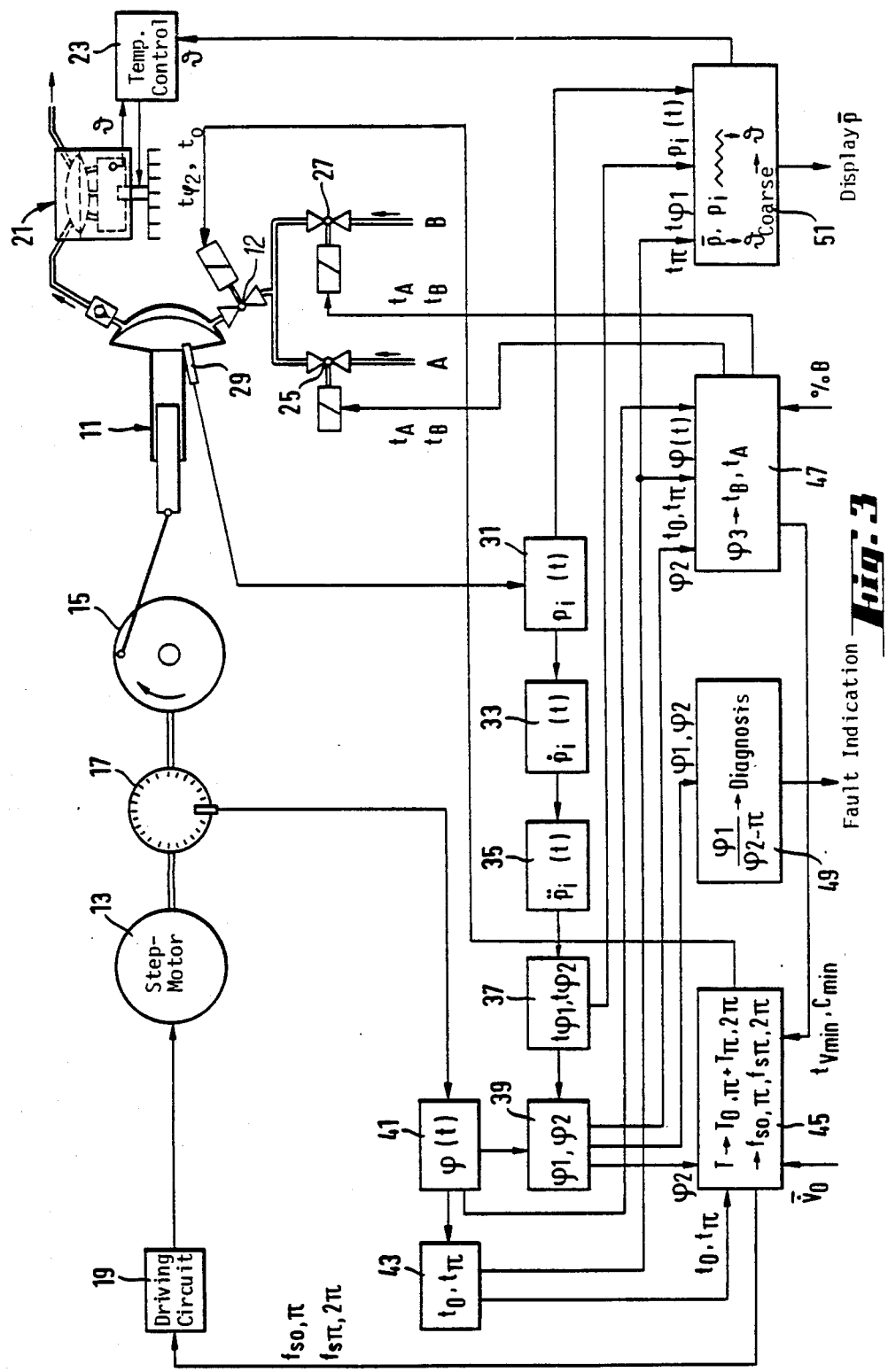
FIG. 3 is a block diagram of a metering pump and a measurement and control apparatus constructed according to the preferred embodiment of the present invention.

FIG. 3 shows an assembly constructed according to a preferred embodiment of the present invention, comprising a pump, a controller for controlling the flow rate and a controller for controlling the mixing ratio of two liquid components.

A piston/diaphragm pump 11 has a conventional output check valve and an externally controlled input valve 12. Pump 11 is driven by a step motor 13 via a crankshaft 15. The angular position of crankshaft 15 is detected by a shaft angle encoder 17. Step motor 13 is driven by a driving circuit 19.

A pulsation damper 21 having temperature control 23 (see below for details) is provided at the output side of pump 11. On the input side of pump 11 there are two proportioning valves 25 and 27 for two liquids components A and B, respectively. The internal pressure within pump 11 is measured by means of a pressure detector 29.

Pressure detector 29 is connected to a pressure signal generator 31 which is connected to a phase transition detector 39 via differentiating circuits 33 and 35 and a zero crossing detector 37. Shaft angle encoder 17 is connected to an angle signal generator 41 which is connected to a dead center detector 43. Evaluation and control circuits 45, 47, 49, and 51 receive selected signals from the aforementioned detectors and signal generators 31, 37, 39, 41, and 43 and generate display and control signals. The dynamic measurement of the internal pressure $p_i(t)$ within piston/diaphragm pump 11 can be performed within the working liquid volume or directly within the pumping chamber by means of a pressure detector with a small dead volume and a welded detector membrane having a sufficiently high resonant frequency (e.g., >5 kHz for a pump stroke frequency of about 5-10 Hz).

The angular position $\phi(t)$ of crankshaft 15 is measured by means of shaft angle encoder 17 which, preferably, operates optoelectronically and has a graduated circle resolution of better than 1:500. Bottom dead center (beginning of the compression portion) is defined as $\phi = 0$. The pressure signal $\bar{p}_i(t)$ is amplified by pressure signal generator 31 and is differentiated twice by differentiating circuits 33 and 35. From the second derivative $\ddot{p}_i(t)$ the instants in time of crankshaft 15 angular locations $\phi_1$ and $\phi_2$ are located by means of zero crossing detector 37 which may be embodied as an edge triggered detector. From said instants in time, phase transition detector 39 derives the phase angles $\phi_1$ and $\phi_2$ from the output signal of angle signal generator 41.

Evaluation and control circuit 45 controls step motor 13 of pump 11. According to the control algorithm of equation (1), time T (for a full turn of crankshaft 15) is derived from nominal mean aspiration flow rate $\bar{V}_o$ and $\phi_2$. Since equation (1) contains no requirement as to the kind of movement between 0 and $2\pi$ this movement is optimized with regard to convenient conditions for the control of proportioning valves 25 and 27 and the pulsation damping. Specifically, T is divided into two time intervals, namely $T_{o,\pi}$ and $T_{\pi,2\pi}$, where $$T_{o,\pi} + T_{\pi,2\pi} = T$$

The step frequency $f_s$ of step motor 13 is derived from these time intervals as follows $$f_{so,\pi} = \frac{N}{2T_{o,\pi}} \text{ and } f_{s\pi,2\pi} = \frac{N}{2T_{\pi,2\pi}}$$

where N is the number of steps for a full turn of step motor 13. T is divided into $T_{o,\pi}$ and $T_{\pi,2\pi}$ as follows: Assume $C_{min}$ is the desired minimum concentration of one of the components A and B in the mixture and assume $t_{Vmin}$ is the fastest opening time which may be realized with proportioning valves 25 and 27. This results in the following requirement for reliable operation of proportioning valves 25 and 27:

$$T_{\pi,2\pi} = \frac{\pi t_{Vmin}}{2C_{min}}$$

This equation is related to the worst case in which the opening time of the proportioning valve delivering the lesser amount of the components lies near $\phi \approx 1.5\pi$ On the other hand, with regard to an optimal pulsation damping it is desirable to have the interval $T_{o,\pi}$ (which includes the feed portion) be as long as possible. Thus, $T_{\pi,2\pi}$ is always selected as stated in the equation above. This leads to the following equations for step motor drive 13:

$$T_{o,\pi} = \frac{0.5 \, V_d}{\bar{V}_o} (1 - \cos \phi_2) - \frac{\pi t_{Vmin}}{2C_{min}} \text{ and } f_{so,\pi} = \frac{N}{2T_{o,\pi}} \quad (1a)$$

$$T_{\pi,2\pi} = \frac{\pi t_{Vmin}}{2C_{min}} \text{ and } f_{s\pi,2\pi} = \frac{N}{2T_{\pi,2\pi}}. \quad (1b)$$

Thus, the aspiration portion of the total cycle lasts only as long as necessary so that a sufficiently accurate operation of proportioning valves 25 and 27 is assured. Consequently, the duration of the feed portion is then maximized which leads to a better pulsation damping of the liquid flow, particularly if the flow rate is small indicating a long period T.

Evaluation and control circuit 45 delivers a signal for opening input valve 12 at the end of the decompression portion, time $t_2$. Circuit 45 also delivers a signal for closing input valve 12 at time $t_o$.

Evaluation and control circuit 47 controls proportioning valves 25 and 27, i.e., the mixture ratio of liquid components A and B or the volume concentration %B in (A+B), respectively. Circuit 47 first derives time $t_\pi$ at which crankshaft 15 passes top dead center from signal $\phi(t)$ and at time $t_\pi$ proportioning valve 25 is opened and proportioning valve 27 is closed. The value of $\phi_3$ is known from application of the control algorithm of equation (2) to $\phi_2$ and the determined nominal value of the volume concentration %B. By correlating $\phi_3$ with $\phi(t)$ the valve switching time $t_3$ is derived and at this instant proportioning valve 27 is opened and proportioning valve 25 is closed.

Evaluation circuit 49 operates to detect faults in the pump valves, etc. For this purpose the ratio $\phi_1/(\phi_2 - \pi)$ is calculated which must be within a certain range characteristic of the pump design. If this range is substantially exceeded, i.e., the feed portion is substantially shorter and/or the aspiration portion is substantially longer than expected, then this is an indication of either aspirated air bubbles or of a badly closing input valve 12. If the ratio is less than the characteristic range, then this is an indication of a badly closing output valve. Evaluation circuit 49 then generates a suitable fault indication signal.

Evaluation and control circuit 51 calculates, from the average feed pressure $\bar{p}$ occuring during a number of cycles (e.g., n=5), the temperature necessary for pressure compensation in the volume of pulsation damper 21.

For equalization (pulsation damping) of the liquid flow of metering pumps it is well known to use devices having a volume through which the liquid flows and in which said volume is enlarged proportional to increasing feed pressure and reduced proportional to decreasing feed pressure ($\Delta V = C \Delta p$). Such devices are the hydraulic analogs of electrical capacitors. When used in liquid chromatography with programmable mixing gradient devices on the aspiration side of a pump these conventional devices are disadvantageous in that the volume at high pressure is enlarged to such an extent that substantial time delays occur between the state of the program of the mixing arrangement and the actual mixing ratio delivered at the output of the damping device, especially at low flow rates. Moreover, a variation in the flow resistance causes a variation of this time delay and thus causes a degradation of analysis reproducibility.

Figure 4:
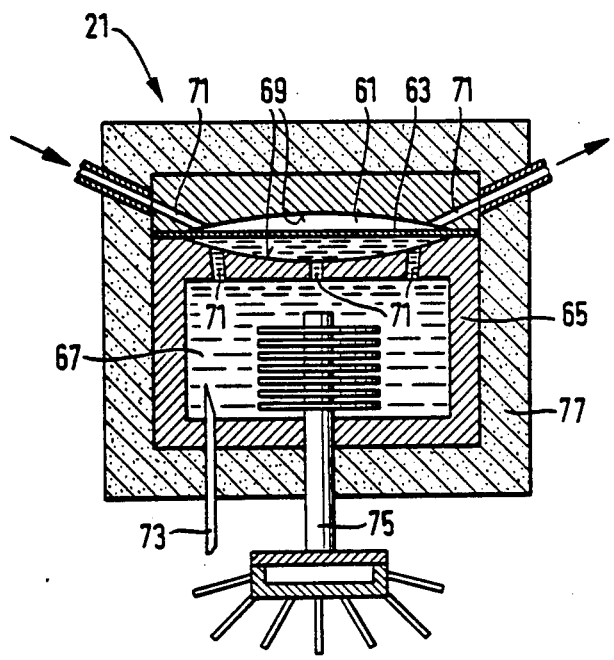
FIG. 4 is a detailed cross-section of a pulsation damper employed in the arrangement depicted in FIG. 3.

FIG. 4 shows in detail pulsation damper 21 as employed in the arrangement of FIG. 3. Damping volume 61, through which the pumped liquid flows, is separated by an elastic steel diaphragm 63 from an elastic liquid 67 which is enclosed between a pressure resistant housing 65 and diaphragm 63. Liquid 67 has a compressibility $\mathscr{X}(p)$ and a thermal expansion coefficient $\mathscr{X}$. Diaphragm 63 is secured against overstress (due to operating faults) by means of two spheric abutments 69 having inlet and outlet bores 71. As the pressure in damping volume 61 increases, the enclosed liquid 67 is compressed and diaphragm 63 bends towards liquid 67 thus causing an enlargement of volume 61. This is a desired effect since the enlargement corresponds to the liquid volume maximally delivered by pump 11 during one cycle. Pulsation damper 21 stores a part of the volume delivered by pump 11 during the feed portion and outputs this part of the volume during the remaining (non-productive) segment of the cycle. The above-described damper 21 differs from conventional embodiments in that the possible movement of diaphragm 63 in the above-described example is limited by abutments 69 to about four times the volume normally stored. A further difference from conventional embodiments is that the temperature $\theta$ of the enclosed liquid 67 is quickly controlled (transition time of about 1–2 minutes) in such a manner that diaphragm 63 moves about its neutral position independent of the average feed pressure $\bar{p}$. This is accomplished by the following relationship:

$$\theta = \frac{1}{\gamma} \int_0^{\bar{p}} \mathscr{X}(p)\,dp \tag{3}$$

For this purpose pulsation damper 21, shown in FIG. 4, includes a temperature sensor 73 and a Peltier heating/cooling element 75. Additionally, the whole of pulsation damper 21 is enclosed within a heat isolating coating 77.

Evaluation and control circuit 51, shown in FIG. 3, uses equation (3) for a coarse computation of the temperature required for pressure compensation of damping volume 61. Fine adjustment of this computation is accomplished by determining the temperature at which the remaining pulsation $p_{i\eta}$ of the pressure, measured between angles $\phi_1$ and $\pi$, reaches a minimum, i.e., the temperature at which the diaphragm is free to move an amount sufficient for receiving the volume of liquid delivered per cycle by the pump. Evaluation and control circuit 51 thus derives the following data:

$$\frac{1}{n} \sum_{(n)} \left( \frac{1}{t_\pi - t_{\phi 1}} \int_{t_{\phi 1}}^{t_\pi} p_i dt \right) = \bar{p}$$

From this result $\theta_{coarse}$ is obtained according to equation (3). Furthermore:

$$p_{it\pi} - p_{it\phi 1} = p_{i\eta}$$

From this, $\theta$ is finely adjusted until $p_{i\eta}$ passes through a minimum. For best results, $\theta_{coarse}$ is selected so that a pressure is obtained in liquid volume 61 which is too high for optimal damping. Then, by means of fine regulation, pulsation minimum $p_{i\eta min}$ is adjusted and the nominal temperature value belonging thereto is stored. If $\bar{p}$ is changed afterwards a new nominal temperature value is derived according to equation (3), etc. Thus, the system is self-calibrating with regard to the temperature necessary for optimal damping so that there are no particular requirements as to the absolute accuracy of the temperature measuring and controlling arrangement.

I claim:

1. A pump for pumping a compressible liquid at a mean aspiration flow rate, the pump having a reciprocal pumping cycle including an aspiration portion, a compression portion, a feed portion and a decompression portion, the pump comprising:
    a chamber for containing the liquid, said chamber having a stroke volume;
    a piston, slidably engaged within the chamber, for exerting an internal pressure on the liquid;
    driving means, coupled to the piston, for causing the piston to move reciprocally within the chamber at a stroke frequency;
    encoder means, coupled to the piston, for measuring the instantaneous angular position of the piston and for generating an angle signal indicative of said position;
    pressure detector means, coupled to the chamber, for measuring the instantaneous internal pressure of the chamber and for generating a pressure signal indicative thereof;
    logic means, coupled to the encoder means and to the pressure detector means, for receiving the angle and pressure signals and for determining an aspiration angle, $\phi_2$, at which a transition between the decompression and aspiration portions occurs; and
    control means, coupled to the logic means and to the driving means, for receiving the aspiration phase angle and, responsive thereto, for causing the driving means to vary the stroke frequency such that the mean aspiration flow rate is maintained substantially equal to a desired rate.

2. A pump as in claim 1, wherein the control means is operative for varying the stroke frequency substantially in accordance with $$T = \frac{0.5\, \hat{V}_d}{\bar{V}_o} (1 - \cos \phi_2)$$

wherein T is the inverse of the stroke frequency, $\hat{V}_d$ is the stroke volume and $\bar{V}_o$ is the desired rate.

3. A pump as in claim 2, wherein:
    the pressure detector means is operative for taking the second time derivative of the instantaneous internal pressure of the chamber and the pressure signal is indicative of the second time derivative;
    zero crossing detector means is coupled between the pressure detector means and the logic means and is operative for receiving the pressure signal and for generating a crossing signal indicative of a zero crossing thereof; and
    the logic means is operative for receiving the angle and crossing signals and for determining the aspiration phase angle therefrom.

4. A pump as in claim 3, further comprising:
    first and second containers for containing first and second liquids, respectively; and
    proportioning means, connected to the first and second containers and to the chamber, for selectively connecting the first and second containers to the chamber and for switching between the first and second containers at a switching phase angle, $\phi_3$, substantially equal to $$\phi_3 = -\arccos\left[\frac{\% B(\cos \phi_2 - 1)}{100} + 1\right] + 2\pi$$

wherein %B is a volume percentage of the second liquid.

5. A pump as in claim 4, wherein the measuring means is futher operative for measuring a feed phase angle, $\phi_1$, at which a transition between the compression and feed portions occurs; and further comprising an evaluation means, coupled to the measuring means, for generating a fault indication if the aspiration phase angle or the feed phase angle is beyond an expected range.

6. A pump as in claim 5, further comprising:
a damping chamber, connected to the chamber and containing a damping liquid, for receiving the pumped liquid;
a diaphragm, within the damping chamber, for maintaining separate the damping liquid and the pumped liquid;
heater means, located within the damping liquid, for setting a temperature of the damping liquid; and
heater control means, coupled to the heater means, for controlling the temperature of the damping liquid such that pulsations in the pumped liquid are damped.

7. A pump as in claim 6, wherein the heater means comprises a Peltier heating and cooling element.

8. A pump for pumping a liquid at a mean flow rate, the pump having a reciprocal pumping cycle including an aspiration portion, a comprssion portion, a feed portion and a decompression portion, the pump comprising:
a chamber for containing the liquid, said chamber having a stroke volume;
a piston, slidably engaged within the chamber, for exerting an internal pressure on the liquid;
driving means, coupled to the piston, for causing the piston to move reciprocally within the chamber at a stroke frequency;
measuring means, coupled to the chamber and to the piston, for measuring a feed phase angle, $\phi_1$, at which a transition between the compression and feed portions occurs; and
control means, coupled to the measuring means and to the driving means, for receiving the measurement and, responsive thereto, for causing the driving means to vary the stroke frequency such that the mean feed flow rate is maintained substantially equal to a desired rate;
wherein the control means is operative for varying the stroke frequency substantially in accordance with $$T = \frac{0.5 \hat{V}_d}{\overline{V}_p}(1 - \cos \phi_2)$$

wherein T is the inverse of the stroke frequency, $\hat{V}_d$ is the stroke volume and $\overline{V}_p$ is the desired rate; and
wherein the measuring means comprises:
encoder means, coupled to the piston, for measuring the instantaneous angular position of the piston and for generating an angle signal indicative of said position;
pressure detector means, coupled to the chamber, for measuring the instantaneous internal pressure of the chamber and for generating a derivative signal indicative of the second time derivative thereof;
zero crossing detector means, coupled to the pressure detector means, for receiving the derivative signal and for generating a crossing signal indicative of a zero crossing thereof; and
logic means, coupled to the encoder means and to the zero crossing detector means, for receiving the angle and crossing signals and for determining the feed phase angle therefrom.

9. A pump as in claim 8, further comprising an evaluation means, coupled to the measuring means, for generating a fault indication if the aspiration phase angle or the feed phase angle is beyond an expected range.

10. A pump as in claim 9, further comprising:
a damping chamber, connected to the chamber and containing a damping liquid, for receiving the pumped liquid;
a diaphragm, within the damping chamber, for maintaining separate the damping liquid and the pumped liquid;
heater means, located within the damping liquid, for setting a temperature of the damping liquid; and
heater control means, coupled to the heater means, for controlling the temperature of the damping liquid such that pulsations in the pumped liquid are damped.

11. A pump as in claim 10, wherein the heater means comprises a Peltier heating and cooling element.

* * * * *

UNITED STATES PATENT AND TRADEMARK OFFICE
CERTIFICATE OF CORRECTION

PATENT NO. : 4,624,625

DATED : November 25, 1986

INVENTOR(S) : Helge Schrenker

It is certified that error appears in the above-identified patent and that said Letters Patent is hereby corrected as shown below:

Column 1, line 26, "Thus, the feed pumping" should read -- Thus, the actual feed portion --

Column 4, line 7, "pumping pressure;" should read -- feed pressure; --

Column 4, line 11 and 12, "illustrated embodiment" should read -- illustrated preferred embodiment --

Column 5, line 28, "feed flow" should read -- chamber flow --

Column 6, line 41, "valve proportioning" should read -- proportioning valve --

Column 11, line 6, "futher" should read -- further --

Signed and Sealed this

Twenty-seventh Day of October, 1987

Attest:

DONALD J. QUIGG

Attesting Officer    Commissioner of Patents and Trademarks